United States Patent
Lahr

(10) Patent No.: US 8,752,073 B2
(45) Date of Patent: Jun. 10, 2014

(54) GENERATING EVENT DEFINITIONS BASED ON SPATIAL AND RELATIONAL RELATIONSHIPS

(75) Inventor: Nils B. Lahr, Snoqualmie, WA (US)

(73) Assignee: Orions Digital Systems, Inc., Snoqualmie, WA (US)

( * ) Notice: Subject to any disclaimer, the term of this patent is extended or adjusted under 35 U.S.C. 154(b) by 198 days.

(21) Appl. No.: 13/471,302

(22) Filed: May 14, 2012

(65) Prior Publication Data

US 2012/0291051 A1 Nov. 15, 2012

Related U.S. Application Data

(60) Provisional application No. 61/486,133, filed on May 13, 2011.

(51) Int. Cl.
*G06F 3/00* (2006.01)

(52) U.S. Cl.
USPC .......................................................... 719/318

(58) Field of Classification Search
USPC .......................................................... 719/318
See application file for complete search history.

(56) References Cited

U.S. PATENT DOCUMENTS 7,272,490 B2 * 9/2007 Imasaki et al. ................. 701/517
8,300,884 B2 * 10/2012 Sharma .......................... 382/100

OTHER PUBLICATIONS

David, An Event-Based Architecture Definition Language, Sep. 1995.*

* cited by examiner

*Primary Examiner* — Lechi Truong
(74) *Attorney, Agent, or Firm* — Lee & Hayes, PLLC

(57) ABSTRACT

Data from one or more sensors are used to detect an event corresponding to an activity by a person. The detection of the event is then used to loosely model the event to produce an initial event definition. The initial event definition is used in searching historical sensor data to detect other prospective occurrences of the event. Based on the detection of these additional occurrences, the event definition is refined to produce a more accurate event definition. The resulting refined event definition can then be used with current sensor data to accurately detect when the activity is being carried out. For example, the activity may be the use of a video imaging device for cheating, and a casino can use the refined event definition with video imaging to detect when people are using the video imaging device for such purposes.

1 Claim, 1 Drawing Sheet

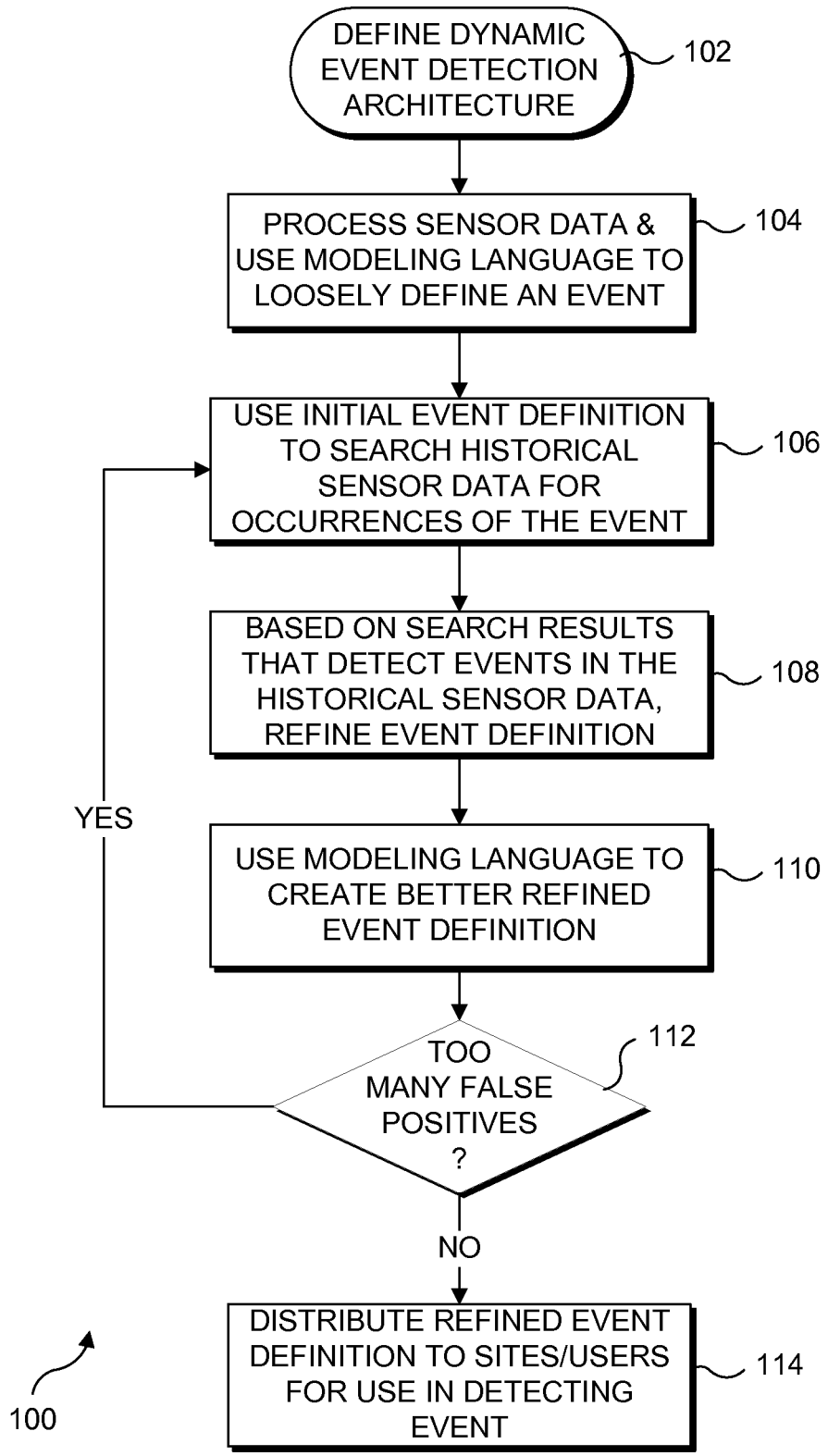

GENERATING EVENT DEFINITIONS BASED ON SPATIAL AND RELATIONAL RELATIONSHIPS

RELATED APPLICATIONS

This application is based on a prior copending provisional application Ser. No. 61/486,133, filed on May 13, 2011, the benefit of the filing date of which is hereby claimed under 35 U.S.C. §119(e).

BACKGROUND

There are many difficulties in identifying complex events, such as recognizing a set of specific human behaviors combined with interactions with inanimate objects. At the same time, the amount of digital data being produced with meaningful event data is increasing exponentially. A single location today can have 6,000 video feeds and 3,000 microphones or highly sensitive air sensors. Timely detection of meaningful events can be helpful in a number of ways, including saving lives and resources.

Today's solutions are incremental additions to existing methodologies. The primary solution is to have a Network Operating System (NOC), which is located physically near the appropriate sensor devices. Video feeds are typically viewed randomly by a 24/7 security staff. Some products can be installed to provide basic object detection, such as facial recognition, which in turn helps the security staff identify locations to investigate.

The field of object recognition has not advanced sufficiently to enable highly accurate detection of relevant data in real-time. Available systems come with the object detection systems built into the system, and today, there are only a few that are used for event detection. One issue that arises is that aspects of the object detection need to be defined prior to selling and deploying a product. Lack of confidence factors in object detection has led to an adversity in connecting multiple events, such as human behavior to specific usage of an identified object. Additionally, these events and behaviors may change rapidly over time, so that detection systems become quickly outdated. Because of the complexity in creating a framework around detecting objects, the best known generic system in widespread use is facial recognition. However, these systems have difficulty in processing images and providing highly accurate results in real-time. As new types of threats or actions are identified, these systems fall short of their ability to detect these new types of events. Due to the volume of real-time data, existing systems are used more in a forensics situation, rather than in attempting to provide real-time event data across most or all available feeds.

SUMMARY

This application specifically incorporates by reference the disclosure of the provisional patent application identified above as a related application.

The present approach relates to utilizing most or all available data, such as a plurality of video signals, to generate complex definitions of human behavior, spatial events and interconnecting relationships between the two. More specifically, the present invention relates to identifying a complex pattern, such as card counters at a casino using electronic means (e.g., an iPhone™ or other type of video source), creating an event definition to match such activities, and enabling future events to automatically generate notifications. Depending on confidence ratings of an event definition, various actions may be taken. By way of example, initially only iPhone™ users might be part of the definition. Yet the number of iPhone™ users in a casino is too great to have humans review all video of all iPhones™ that match the initial event definition. A group of experts or others could review some or all of these iPhone™ situations by watching only the video pertaining to the iPhone™ usage.

A rating system has been devised to enable logging each video event of an iPhone™ user. As a result, it is possible to sort a large amount of video imaging based on what is most likely cheating, which is differentiated from just normal usage of the iPhone™ in a casino. Then the top suspected iPhone™ video imaging would be further reviewed, and the event definition modified and/or adapted to include various signatures that describe specific methods of cheating in a casino with an iPhone™. This process may be repeated until the event definition is sufficiently generic to catch iPhone™ cheating in a casino, yet specific enough to prevent virtually all normal usage from throwing a false positive of potentially illegal activity. It must be strongly emphasized that this same approach can be applied to other types of actions by people that are detected by other types of sensors, and can be used for many other types of applications, where it is desirable to identify a specific type of conduct.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 is a flowchart illustrating exemplary logic for implementing the approach described below.

DESCRIPTION

Figures and Disclosed Embodiments are not Limiting

Exemplary embodiments are illustrated in the referenced drawing FIGURE. It is intended that the exemplary embodiments and FIGURE disclosed herein are to be considered illustrative rather than restrictive. No limitation on the scope of the technology and of the claim set that follows is to be imputed to the examples shown in the drawing and discussed herein. Further, it should be understood that any feature of one embodiment disclosed herein can be combined with one or more features of any other embodiment that is disclosed, unless otherwise indicated.

In accordance with the present invention, there is provided a highly accurate object detection system combined with an event modeling capability such that complex definitions can be created to recognize a series of events in one or more data streams. A framework of pre-processing is performed such that events and signatures of objects and interactions between them are stored for later use. A plug-in architecture is introduced, enabling a set of event definitions to be loaded and prioritized into a system providing real-time monitoring of all available data feeds of one more types. Rather than focusing on a specific object type, such as faces, this approach focuses on implementing a range of event definitions that can all exist simultaneously. Also, in accordance with the present approach, a combination of automation can be used with human interaction in a cyclic method, so as to increase a range of an event definitions, while also increasing a confidence factor of a match that is identified.

One exemplary embodiment of this invention would be to, for example, setup a pre-processing system at a casino. Initially, with no definitions, the system can convert the video data at the casino into abstract objects, and then create normalized signatures of each object. Although this disclosure does not cover the methods and procedures specific to creating these normalized signatures from a two-dimensional video feed, it assumes such a process exists and is substantially better than existing rasterized methods of object detection. The casino realizes that there is an issue with utilizing software on other computer-based assistance, such as an iPhone™ application, for card counting and that it is difficult to review thousands of video feeds in real-time, as well as decipher users of a legitimate iPhone™ application, versus the card-counting one. Initially, an expert system and/or human users can either create a real-time simulation inside the casino, or take existing footage of many video examples of people using the application to cheat.

In accordance with one exemplary embodiment, this material provide by video imaging would be used by the event modeling system to describe the signatures of an iPhone™ user's card counting or other cheaters. The initial definition would then be sent back to the data system and used in a historical sense, to pull out other possible examples across the archives of available video. Essentially an advanced historical search based on the newly created event definition is generated. The results of this step may be very large (i.e., thousands of hours of video) and still something a single Network Operations Center (NOC) would not be capable of adequately filtering. As per this exemplary embodiment of the present approach, the video is distributed in small units of work across the Internet to trained individuals, who can review and rate each event based on the intended match. The results from this work distribution are returned and the modeling language used to refine the event definition. This process may continue until the confidence rating is sufficiently high and/or the number of matches is sufficiently low that the final definition can raise notifications to which an always available NOC can respond accordingly.

As new events, or in most cases threats, arise, the methods and procedures within this approach are applied to generate a new event definition. Then, the new event definition is potentially distributed via a centralized service, such that all organizations with the system installed could benefit from each new definition. The world is an ever changing system and thus, the event definitions will be evolving over time as well.

One exemplary process derived from this approach is shown in FIG. 1 and is described below:

1. Define dynamic event detection architecture;
2. New event occurs (event=complex interaction of movement, object, etc.);
3. Video has been pre-processed enabling historical "matching" in a timely fashion;
4. Modeling language is used to loosely define the event, which becomes the "event definition;"
5. The event definition is then used to search the historical video;
6. If the event definition returns too much video to readily process, units of the video are sent to a distributed work force that is running specialized software to rate the validity of each event match, such that the feedback from the work force becomes the input to create a new, more accurate event definition;
7. The modeling language is used to create a better event definition, but if it still produces too many false positives, steps 5-7 are repeated; and
8. Once the event definition is sufficiently accurate, it is distributed to locations and/or users subscribing to updated event definitions of that type.

As new events become critical to a business, this system will continue to build an archive of definitions, yet remain sufficiently agile to incorporate new definitions over time.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for generating event definitions to identify an event corresponding to an activity, comprising:
    (a) defining a dynamic event detection architecture;
    (b) generally specifying an event that may correspond to the activity;
    (c) processing historical sensor data to detect at least one instance of the event that was generally specified;
    (d) using modeling language derived from the historical sensor data for the at least one instance to create an initial event definition for the event;
    (e) using the initial event definition to search the historical sensor data for additional occurrences of the event;
    (f) based on the additional occurrences of the event that were identified in the search of the historical sensor data, creating a refined event definition; and
    (g) using the refined event definition to detect an activity corresponding to the event.

* * * * *